US008036748B2

(12) United States Patent
Zdeblick et al.

(10) Patent No.: US 8,036,748 B2
(45) Date of Patent: Oct. 11, 2011

(54) INGESTIBLE THERAPY ACTIVATOR SYSTEM AND METHOD

(75) Inventors: Mark Zdeblick, Portola Valley, CA (US); Marc Jensen, Los Gatos, CA (US); Olivier Colliou, Los Gatos, CA (US); Angela Strand, San Francisco, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 0 days.

(21) Appl. No.: 12/665,111

(22) PCT Filed: Nov. 13, 2009

(86) PCT No.: PCT/US2009/064472
§ 371 (c)(1),
(2), (4) Date: Dec. 17, 2009

(87) PCT Pub. No.: WO2010/057049
PCT Pub. Date: May 20, 2010

(65) Prior Publication Data
US 2010/0312228 A1    Dec. 9, 2010

Related U.S. Application Data

(60) Provisional application No. 61/114,442, filed on Nov. 13, 2008.

(51) Int. Cl.
*A61N 1/00*    (2006.01)
*A61K 9/22*    (2006.01)
(52) U.S. Cl. ...................................... 607/30; 604/890.1
(58) Field of Classification Search ............... 604/890.1, 604/131–135, 93.01, 95, 54, 57; 607/9, 17, 607/22, 27, 30
See application file for complete search history.

(56) References Cited

U.S. PATENT DOCUMENTS

| 3,607,788 A | 9/1971 | Adolph |
| 3,642,008 A | 2/1972 | Bolduc |
| 3,679,480 A | 7/1972 | Brown et al. |
| 3,719,183 A | 3/1973 | Schwartz |
| 3,828,766 A | 8/1974 | Krasnow |
| 3,989,050 A | 11/1976 | Buchalter |

(Continued)

FOREIGN PATENT DOCUMENTS

EP    1246356    10/2002

(Continued)

OTHER PUBLICATIONS

Arshak et al., A Review and Adaptation of Methods of Object Tracking to Telemetry Capsules IC-Med (2007) vol. 1, No. 1, Issue 1, pp. 35 of 46.

(Continued)

*Primary Examiner* — Theodore Stigell
*Assistant Examiner* — William Carpenter
(74) *Attorney, Agent, or Firm* — Bozicevic, Field & Francis LLP; Bret E. Field

(57) ABSTRACT

An ingestible therapy activator system and method are provided. In one aspect, the ingestible therapy activator includes an ingestible device having an effector module to send an effector instruction and a responder module associated with a therapeutic device. The responder module may receive and process the effector instruction, resulting in a response by the therapeutic device. Examples of responses by therapeutic device include activating a therapy, deactivating a therapy, modulating a therapy, and discontinuing a therapy.

10 Claims, 5 Drawing Sheets

U.S. PATENT DOCUMENTS

| | | |
|---|---|---|
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester et al. |
| 4,166,453 A | 9/1979 | McClelland |
| 4,239,046 A | 12/1980 | Ong |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,494,950 A | 1/1985 | Fischell |
| 4,559,950 A | 12/1985 | Vaughan |
| 4,635,641 A | 1/1987 | Hoffman |
| 4,654,165 A | 3/1987 | Eisenber |
| 4,669,479 A | 6/1987 | Dunseath |
| 4,725,997 A | 2/1988 | Urquhart et al. |
| 4,763,659 A | 8/1988 | Dunseath |
| 4,784,162 A | 11/1988 | Ricks |
| 4,793,825 A | 12/1988 | Benjamin et al. |
| 4,844,076 A | 7/1989 | Lesho |
| 4,896,261 A | 1/1990 | Nolan |
| 4,975,230 A | 12/1990 | Pinkhasov |
| 4,987,897 A | 1/1991 | Funke |
| 5,016,634 A | 5/1991 | Vock et al. |
| 5,079,006 A | 1/1992 | Urguhart |
| 5,167,626 A | 12/1992 | Casper |
| 5,176,626 A | 1/1993 | Soehendra |
| 5,261,402 A | 11/1993 | DiSabito |
| 5,263,481 A | 11/1993 | Axelgaard et al. |
| 5,281,287 A | 1/1994 | Lloyd |
| 5,283,136 A | 2/1994 | Peled et al. |
| 5,318,557 A | 6/1994 | Gross |
| 5,394,882 A | 3/1995 | Mawhinney |
| 5,458,141 A | 10/1995 | Neil et al. |
| 5,485,841 A | 1/1996 | Watkin et al. |
| 5,596,302 A | 1/1997 | Mastrocola et al. |
| 5,634,468 A | 6/1997 | Platt |
| 5,645,063 A | 7/1997 | Straka et al. |
| 5,740,811 A | 4/1998 | Hedberg |
| 5,792,048 A | 8/1998 | Schaefer |
| 5,802,467 A | 9/1998 | Salazar |
| 5,833,716 A | 11/1998 | Bar-Or |
| 5,845,265 A | 12/1998 | Woolston |
| 5,862,803 A | 1/1999 | Besson |
| 5,868,136 A | 2/1999 | Fox |
| 5,925,030 A | 7/1999 | Gross et al. |
| 5,957,854 A | 9/1999 | Besson |
| 5,974,124 A | 10/1999 | Schlueter, Jr. et al. |
| 5,999,846 A | 12/1999 | Pardey et al. |
| 6,038,464 A | 3/2000 | Axelgaard et al. |
| 6,042,710 A | 3/2000 | Dubrow |
| 6,047,203 A | 4/2000 | Sackner |
| 6,081,734 A | 6/2000 | Batz |
| 6,095,985 A | 8/2000 | Raymond et al. |
| 6,122,351 A | 9/2000 | Schlueter, Jr. et al. |
| 6,141,592 A | 10/2000 | Pauly |
| 6,200,265 B1 | 3/2001 | Walsh et al. |
| 6,206,702 B1 | 3/2001 | Hayden et al. |
| 6,217,744 B1* | 4/2001 | Crosby .................. 205/775 |
| 6,231,593 B1 | 5/2001 | Meserol |
| 6,245,057 B1 | 6/2001 | Sieben et al. |
| 6,285,897 B1 | 9/2001 | Kilcoyne et al. |
| 6,287,252 B1 | 9/2001 | Lugo |
| 6,289,238 B1 | 9/2001 | Besson |
| 6,315,719 B1 | 11/2001 | Rode et al. |
| 6,358,202 B1 | 3/2002 | Arent |
| 6,364,834 B1 | 4/2002 | Reuss |
| 6,366,206 B1* | 4/2002 | Ishikawa et al. ........... 340/573.1 |
| 6,371,927 B1 | 4/2002 | Brune |
| 6,374,670 B1 | 4/2002 | Spelman |
| 6,380,858 B1 | 4/2002 | Yarin et al. |
| 6,394,997 B1 | 5/2002 | Lemelson |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,477,424 B1 | 11/2002 | Thompson et al. |
| 6,496,705 B1 | 12/2002 | Ng et al. |
| 6,526,315 B1 | 2/2003 | Inagawa |
| 6,544,174 B2 | 4/2003 | West |
| 6,564,079 B1 | 5/2003 | Cory |
| 6,577,893 B1 | 6/2003 | Besson |
| 6,579,231 B1 | 6/2003 | Phipps |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,643,541 B2 | 11/2003 | Mok |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,800,060 B2 | 10/2004 | Marshall |
| 6,801,137 B2 | 10/2004 | Eggers et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,046,649 B2 | 5/2006 | Awater et al. |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |

| | | |
|---|---|---|
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams |
| 7,413,544 B2 | 8/2008 | Kerr |
| 7,414,534 B1 * | 8/2008 | Kroll et al. ............... 340/573.1 |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,575,005 B2 | 8/2009 | Mumford |
| 7,616,111 B2 | 11/2009 | Covannon |
| 7,617,001 B2 | 11/2009 | Penner et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,756,587 B2 | 7/2010 | Penner et al. |
| 7,809,399 B2 | 10/2010 | Lu |
| 7,844,341 B2 | 11/2010 | Von Arx et al. |
| 2001/0027331 A1 | 10/2001 | Thompson |
| 2001/0044588 A1 | 11/2001 | Mault |
| 2001/0051766 A1 | 12/2001 | Gazdzinski |
| 2002/0002326 A1 | 1/2002 | Causey et al. |
| 2002/0026111 A1 | 2/2002 | Ackerman |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115517 A1 | 6/2004 | Fukada et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0148883 A1 | 7/2005 | Boesen |
| 2005/0154428 A1 | 7/2005 | Bruinsma |

| Publication No. | Date | Name |
|---|---|---|
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0036134 A1 | 2/2006 | Tarassenko et al. |
| 2006/0061472 A1 | 3/2006 | Lovoi et al. |
| 2006/0065713 A1 | 3/2006 | Kingery |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0280227 A1 | 12/2006 | Pinkney |
| 2006/0280277 A1 | 12/2006 | Tashiro et al. |
| 2006/0282001 A1 | 12/2006 | Noel |
| 2006/0289640 A1* | 12/2006 | Mercure et al. ............... 235/435 |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1* | 5/2007 | Euliano et al. ............... 600/407 |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowshi |
| 2008/0020037 A1 | 1/2008 | Robertson et al. |
| 2008/0021519 A1 | 1/2008 | De Geest |
| 2008/0021521 A1 | 1/2008 | Shah |
| 2008/0027679 A1 | 1/2008 | Shklarski |
| 2008/0033273 A1 | 2/2008 | Zhou |
| 2008/0046038 A1 | 2/2008 | Hill |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0137566 A1 | 6/2008 | Marholev |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1* | 12/2008 | Robertson et al. ....... 340/539.12 |
| 2009/0009332 A1 | 1/2009 | Nunez et al. |
| 2009/0024045 A1 | 1/2009 | Prakash |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |

| | | |
|---|---|---|
| 2009/0076343 A1 | 3/2009 | James |
| 2009/0082645 A1* | 3/2009 | Hafezi et al. ............... 600/302 |
| 2009/0088618 A1 | 4/2009 | Ameson |
| 2009/0099435 A1 | 4/2009 | Say et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0295548 A1 | 12/2009 | Ronkka |
| 2009/0296677 A1 | 12/2009 | Mahany |
| 2009/0303920 A1 | 12/2009 | Mahany |
| 2009/0312619 A1 | 12/2009 | Say et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0010330 A1 | 1/2010 | Rankers |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia |
| 2010/0069002 A1 | 3/2010 | Rong |
| 2010/0081894 A1* | 4/2010 | Zdeblick et al. ............... 600/302 |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0185055 A1 | 7/2010 | Robertson |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0298730 A1 | 11/2010 | Tarassenko et al. |
| 2010/0312580 A1 | 12/2010 | Tarassenko et al. |

FOREIGN PATENT DOCUMENTS

| | | |
|---|---|---|
| EP | 1789128 | 5/2007 |
| EP | 2143369 | 1/2010 |
| WO | 8802237 | 4/1988 |
| WO | WO8802237 | 4/1988 |
| WO | WO9308734 | 5/1993 |
| WO | WO9319667 | 10/1993 |
| WO | WO9843537 | 10/1998 |
| WO | WO9959465 | 11/1999 |
| WO | WO0033246 | 6/2000 |
| WO | WO0100085 | 1/2001 |
| WO | WO0147466 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO03050643 | 6/2003 |
| WO | WO2004014225 | 2/2004 |
| WO | WO2004039256 | 5/2004 |
| WO | WO2004066834 | 8/2004 |
| WO | WO2004068881 | 8/2004 |
| WO | WO2004109316 | 12/2004 |
| WO | WO2005011237 | 2/2005 |

| | | |
|---|---|---|
| WO | WO2005020023 | 3/2005 |
| WO | WO2005024687 | 3/2005 |
| WO | WO2005047837 | 5/2005 |
| WO | WO2005051166 | 6/2005 |
| WO | WO2005110238 | 11/2005 |
| WO | WO2006027586 | 3/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006104843 | 10/2006 |
| WO | WO2006116718 | 11/2006 |
| WO | WO 2006116718 A2 * | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | 2007036741 | 4/2007 |
| WO | 2007036746 | 4/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007071180 | 6/2007 |
| WO | WO2007096810 | 8/2007 |
| WO | WO2007101141 | 9/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2008008281 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | 2008120156 | 10/2008 |
| WO | WO2008133394 | 11/2008 |
| WO | WO2008134185 | 11/2008 |
| WO | 2009001108 | 12/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | 2010019778 | 2/2010 |
| WO | 2010057049 | 5/2010 |
| WO | WO2010107563 | 9/2010 |
| WO | WO2010135516 | 11/2010 |

OTHER PUBLICATIONS

"ASGE Technology Status Evaluation Report: wireless capsule endoscopy" American Soc. for Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Brock, "Smart Medicine: The Application of Auto-ID Technology to Healthcare" Auto-ID Labs (2002) http://www.autoidlabs.org/uploads/media/MIT-AUTOID-WH-010.pdf.

Delvaux et al., "Capsule endoscopy: Technique and indications" Clinical Gastoenterology (2008) vol. 22, Issue 5, pp. 813-837.

Fawaz et al., "Enhanced Telemetry System using CP-QPSK Band-Pass Modulation Technique Suitable for Smart Pill Medical Application" IFIP IEEE Dubai Conference (N.D.); http://www.asic.fh-offenburg.de/downloads/ePille/IFIP_IEEE_Dubai_Conference.pdf.

Given Imaging, "Agile Patency Brochure" http://www.inclino.no/documents/AgilePatencyBrochure_Global_GMB-0118-01.pdf;(N.D.) 4pp.

Gonzalez-Guillaumin et al., "Ingestible capsule for impedance and pH monitoring in the esophagus" IEEE Trans Biomed Eng. (2007) 54(12: 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Melanson, "Walkers swallow RFID pills for science" Engadget (2008); http://www.engadget.com/2008/07/29/walkers-swallow-rfid-pills-for-science/.

"New 'smart pill' to track adherence" E-Health-Insider (2010) http://www.e-health-insider.com/news/5910/new_'smart_pill'_monitors_medicines.

"RFID "pill" monitors marchers" RFID News (2008) http://www.rfidnews.org/2008/07/23/rfid-pill-monitors-marchers/.

"SensiVida minimally invasive clinical systems" Investor Presentation Oct. 2009 28pp; http://www.sensividamedtech.com/SensiVidaGeneralOctober09.pdf.

Shrivas et al., "A New Platform for Bioelectronics-Electronic Pill", Cummins College, N.D.; http://www.cumminscollege.org/downloads/electronics_and_telecommunication/Newsletters/Current%20Newsletters.pdf.

"The SmartPill Wireless Motility Capsule" SMARTPILL, The Measure of GI Health; http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Swedberg, "University Team Sees Ingestible RFID Tag as a Boon to Clinical Trials" RFID Journal Apr. 27, 2010; http://www.rfidjournal.com/article/view/7560/1.

University of Florida News "Rx for health: Engineers design pill that signals it has been swallowed" (2010) 2pp.; http://news.ufl.edu/2010/03/31/antenna-pill-2/.

Barrie, Heidelberg pH capsule gastric analysis. Texbook of Natural Medicine, (1992), Pizzorno, Murray & Barrie.

Carlson et al., "Evaluation of a non-invasive respiratory monitoring system for sleeping subjects" Physiological Measurement (1999) 20(1): 53.

Heydari et al., "Analysis of the PLL jitter due to power/ground and substrate noise"; IEEE Transactions on Circuits and Systems (2004) 51(12): 2404-16.

Intromedic, MicroCam Innovative Capsule Endoscope Pamphlet. 8 pp (http://www.intromedic.com/en/product/productinfo.asp).

Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

Mackay et al., "Endoradiosonde" Nature, (1957) 1239-1240, 179 Nature Publishing Group.

Mckenzie et al., "Validation of a new telemetric core temperature monitor" J. Therm. Biol. (2004) 29(7-8):605-11.

Minimitter Co. Inc. "Actiheart" Traditional 510(k) Summary. Sep. 27, 2005.

Minimitter Co. Inc. Noninvasive technology to help your studies succeed. Mini Mitter.com Mar. 31, 2009.

Mini Mitter Co, Inc. 510(k) Premarket Notification Mini-Logger for Diagnostic Spirometer. 9-21 (1999).
Mini Mitter Co, Inc. 510(k) Premarket Notification for VitalSense. Apr. 22, 2004.
Minimitter Co. Inc. VitalSense Integrated Physiological Monitoring System. Product Description.
Minimitter Co. Inc. VitalSense Wireless Vital Signs Monitoring. Temperatures.com Mar. 31, 2009.
Mohaverian et al., "Estimation of gastric residence time of the Heidelberg capsule in humans: effect of varying food composition" Gastroenterology (1985) 89:(2): 392-7.
Philips Respironics (http/minimitter.com/products.cfm) Products, Noninvasive Technology to Help Your Studies Succeed. 510(k) Permanent Notification for Vital Sense. Apr. 22, 2004.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Zworkin, "A Radio Pill" Nature, (1957) 898, 179 Nature Publishing Group.
"Smartlife awarded patent for knitted transducer" Innovation in Textiles News: http://www.innovationintextiles.com/articles/208.php; 2pp. (2009).
Gilson, D.R. "Molecular dynamics simulation of dipole interactions", Department of Physics, Hull University, Dec. 2002, p. 1-43.
Li, P-Y, et al. "An electrochemical intraocular drug delivery device", Sensors and Actuators A 143 (2008) p. 41-48.
NPL__AntennaBasics.pdf, p. 1-3.
Santini, J.T. et al, "Microchips as controlled drug delivery-devices", Agnew. Chem. Int. Ed. 2000, vol. 39, p. 2396-2407.
Shawgo, R.S. et al. "BioMEMS from drug delivery", Current Opinion in Solid State and Material Science 6 (2002), p. 329-334.
Soper, S.A. et al. "Bio-Mems Technologies and Applications", Chapter 12, "MEMS for Drug Delivery", p. 325-346.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Description of ePatch Technology Platform for ECG and EMG, located it http://www.madebydelta.com/imported/images/DELTA__Web/documents/ME/ePatch_ECG_EMG.pdf, Dated Sep. 2, 2010.

* cited by examiner

INGESTIBLE THERAPY ACTIVATOR SYSTEM AND METHOD

RELATED APPLICATION AND CROSS REFERENCE

This application claims the benefit of U.S. Provisional Application Ser. No. 61/114,442 filed on Nov. 13, 2008, the entire disclosure of which is incorporated herein by reference.

FIELD OF THE INVENTION

The present invention relates generally to medical therapy systems, devices, and methods. More specifically, the invention relates to systems, devices, and methods for activation and/or modulation of various medical therapies using an ingestible electronic device.

BACKGROUND

Multiple therapies exist for various health-related conditions, events, and defects. Such therapies may be implemented as implanted devices, e.g., cardiac rhythm management devices, neural stimulation/neuromodulation devices, intrathecal drug delivery pumps, and functional neuromodulation prostheses such as cochlear implants, retinal implants, and artificial joints, limbs and organs. Once implanted, however, such devices may not provide the functionality to facilitate controlled activation or modification.

In one example, a neural stimulation device may deliver pain-control therapies to the spinal column, yet the neural stimulation device may not be activated on demand. Stated differently, the neural stimulation device is always activated after implantation. As a result, the patient may be subjected to neural stimulation, as well as its associated unwanted side effects, at times when such therapy is not needed.

In another example, a neural modulation device such as a spinal cord stimulator may provide therapeutic benefit for pain, yet the rate of stimulation may not be adjustable to align stimulation to the patient's lifestyle, e.g., a higher intensity during high activity periods and a lower intensity during low activity periods. As a result, the patient may need to restrict activities which do not conform to the stimulation intensity to receive optimal therapy results or suffer diminished therapy results when engaged in non-conforming activities.

Therefore, it would be desirable to have systems, devices, and methods for controlling therapies, for optimizing therapy results, and for enhancing patient treatment without having limitations placed on the patient.

SUMMARY

The present disclosure includes a system for providing instructions to a therapeutic device. The therapeutic device can be any type of device, such as a cardiac therapeutic device, a neural stimulation device, an intrathecal drug delivery pump, a gastrointestinal device; and a neural stimulation prosthesis. The system includes an ingestible unit and a responder module. The ingestible unit includes an output or effector module that provides an effector instruction to the responder module. The responder module receives and processes the effector instruction and communicates the effector instruction to the therapeutic device to alter the operation of the therapeutic device.

DETAILED DESCRIPTION

Figure 1:
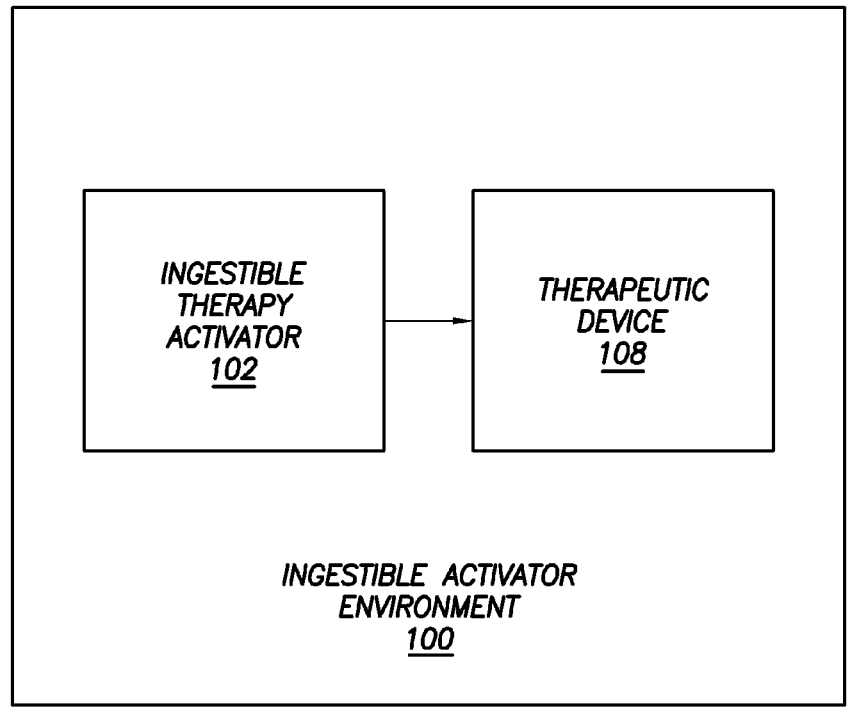
FIG. 1 illustrates an ingestible activator environment including an ingestible therapy activator.

Generally, the invention may provide for controlled activation and/or modulation of an implanted medical device or related therapy. More particularly, the invention includes use of an ingestible device to effect activation and/or modulation of devices/therapies related to implantable medical devices. Typically, the patient controls ingestion of the ingestible device. Ingestion of the ingestible device results in activation and/or modulation of the patient's medical device and/or therapy. Alternatively, ingestion of the ingestible device may inactivate or discontinue a device/therapy. Thus, as a novel and beneficial result of the invention, the patient and/or other party may control at will various outcomes associated with various implanted medical devices and related therapies based on the provision of ingestible devices and a healthcare provider or other party may control a supply, e.g., by prescription, of the ingestible devices.

Use of an ingestible device to activate and/or modulate therapy may have broad potential application for any implanted device or therapy, to include cardiac rhythm management; neural stimulation and/or neuromodulation (sometimes collectively referred to herein as "neural stimulation"); intrathecal drug delivery pumps and therapies; and functional neuromodulation prostheses such as cochlear implants, retinal implants, and artificial joints, limbs and organs.

Activation of therapy includes, for example, activation of a device to induce and event or condition. For example, activation of a gastric banding device having neural stimulation electrodes may induce increased satiety and/or induce an improvement in the rate of stomach motility. Further, the ingestible device may activate the band portion of the gastric banding device, e.g., constricting the band. If the ingestible device is taken prior to ingestion of a meal, the patient may control appetite, satiety, caloric intake, and ultimately influence weight management results, etc.

Certain aspects may be directed to in-body therapies and may include, for example, implantable medical devices. The term "implantable medical device", as used herein, refers to a device configured to be positioned at least partially on a living body, at least partially in a living body, or a combination thereof.

For example, the implantable medical device may include a lead having various electrode configurations communicably associated with controller circuitry, a power source, etc. More particularly and illustratively, the implantable medical device may comprise one or more leads with multiple in-line segmented electrode satellites, wherein each electrode is independently controllable and power/data wire(s) for multiplexing the multiple segmented electrode satellites. Various configurations of devices which may be used in conjunction with this invention may be described/disclosed in the PCT application no. PCT/US2003/039524 published as WO 2004/052182; PCT application No. PCT/US2005/031559 published as WO 2006/029090; PCT application No. PCT/US2005/046811 published as WO 2006/069322; PCT application No. PCT/US2005/046815 published as WO 2006/069323; PCT application No. PCT US2006/048944 published as WO 2007/075974; U.S. application Ser. No. 11/939,524 published as US 2008-0114230 A1.

Various configurations of devices which may be used in conjunction with this invention may be described/disclosed in PCT application Ser. Nos. PCT/US2008/052845 published as WO/2008/095183 and PCT/US2006/016370 published as WO/2006/116718. Each of the aforementioned applications is herein incorporated by reference in its entirety. The aforementioned configurations are for illustrative purposes only and that various other components and configurations are possible.

FIG. 1 illustrates an ingestible therapy activator environment 100 including an ingestible therapy activator 102. In various aspects, the ingestible therapy activator environment may be a living being, such as a mammalian being, including a human being. In various aspects, the ingestible therapy activator 102 may communicably interoperate with one or more therapeutic devices 108, e.g., in-body devices such as implanted devices or other devices. The communicable interaction may result in activation and/or modulation of the therapeutic device, 108, e.g., immediate activation of the therapeutic device 108, delayed activation of the therapeutic device 108, immediate modulation of the therapeutic device 108, delayed modulation of an activity associated with the therapeutic device 108, etc. In this manner, a patient may control a therapeutic outcome via ingestion of the ingestible therapy activator 102.

Figure 2:
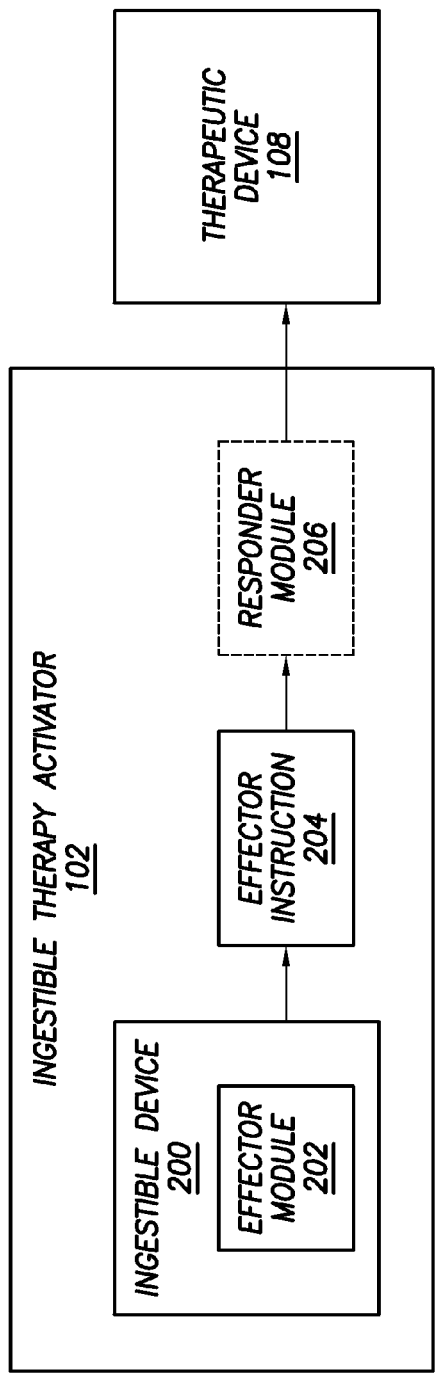
FIG. 2 illustrates the ingestible therapy activator of FIG. 1 in greater detail.

FIG. 2 illustrates the ingestible therapy activator 102 of FIG. 1 in greater detail. In various aspects, the ingestible therapy activator 102 includes an ingestible device 200 having an effector module 202, an effector instruction 204, and, optionally, a responder module 206. Upon ingestion of the ingestible device 200, the effector module 202 may send, e.g., transmit, the effector instruction 204. The effector instruction 204 may be received, e.g., via the responder module 206, and may cause activation and/or modulation of a therapeutic device 108 and/or a therapy associated with the therapeutic device 108. Further, multiple ingestible devices 200 may be ingested simultaneously or in close temporal proximity, and each of the multiple ingested ingestible devices 200 may interact with one or more therapeutic devices 108.

The ingestible device 200 includes any device, component, hardware, and/or software, and combinations thereof, capable of ingestion by a living being and further capable of mechanical, electronic, and/or in communicable interoperation with the effector module 202, described hereinafter.

To illustrate, the ingestible device 200 may include, comprise, be integrated into, etc., a placebo structure. The placebo structure may comprise, for example, a capsule, a pill, etc. To further illustrate, the ingestible device 200 may include, comprise, be integrated into, etc. an ingestible medication. The ingestible medication may comprise, for example, a capsule, a pill, liquid, etc., and may be prescribed, over-the-counter, etc.

Various ingestible devices 200 may comprise, include, be integrated with, etc., devices such as those described in the PCT/US2008/052845 published as WO/2008/095183 and PCT/US2006/016370 published as WO/2006/116718, the entire disclosure of which is incorporated herein by reference. Additionally, all references cited herein are hereby incorporated by reference in their entirety.

A pharma-informatics system described in PCT/US2006/016370, filed Apr. 28, 2006, which includes compositions, includes systems and methods that allow for the detection of the actual physical delivery of a pharmaceutical agent to a body.

An Ionic Emission Module or Ingestible Event Marker (IEM) system described in PCT/US2008/52845, filed Feb. 1, 2008, and U.S. patent application Ser. No. 12/564,017, filed Sep. 21, 2009 (both of which are incorporated herein by reference) include an IEM and a personal signal receiver. Aspects of the IEM include an identifier, which may or may not be present in a physiologically acceptable carrier. The identifier is characterized by being activated upon contact with a target internal physiological site of a body, such as digestive tract internal target site. The personal signal receiver is configured to be associated with a physiological location, e.g., inside of or on the body, and to receive a signal of the IEM. During use, the IEM broadcasts a signal which is received by the personal signal receiver.

Figure 8:
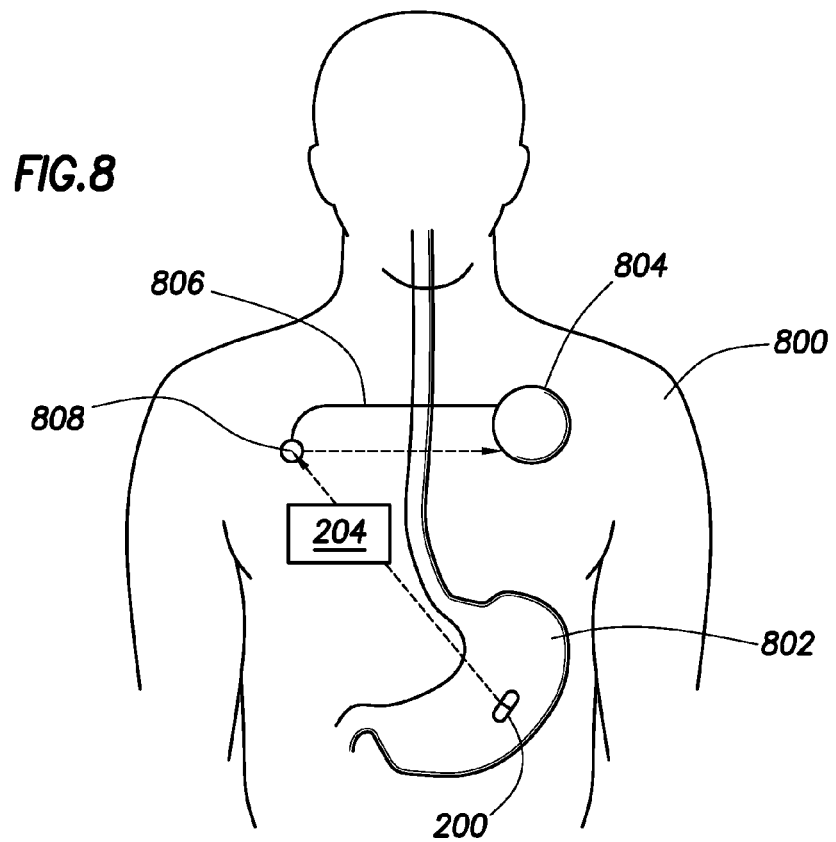
FIG. 8 illustrates ingestion and activation of a therapeutic device via an ingestible therapy activator.

The IEM also includes two dissimilar materials deposited on two sides of the IEM to form electrochemical potentials and act as the cathode and the anode to form a power source. The dissimilar materials may be separated by a non-conducting material or skirt that amplifies the signal through increasing the current path. More specifically, the dissimilar materials can be made of any two materials appropriate for the environment in which the IEM will be operating. For example, when used with the ingestible device the dissimilar materials may be any pair of materials with different electrochemical potentials that are ingestible. An illustrative example includes the instance when the IEM is in contact with an ionic solution such as stomach acids, as shown in FIG. 8 below. Suitable materials are not restricted to metals, and in certain aspects the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable. Additionally, a control module (not shown) is electrically coupled to each of the two dissimilar materials in order to receive power and become activated as well control the conductance and hence the current path between the two dissimilar material. The control module alters conductance between the dissimilar materials in a unique manner. By altering the conductance path between the dissimilar materials, the control module is capable of controlling the magnitude of the current through the conducting fluid/liquid that surrounds the IEM or ingestible device 200. This produces a unique current signature that carries or encodes the effector instruction and can be detected and measured by a receiver, such as the responder module 206, which can be positioned internal or external to the body.

A controlled activation ingestible identifier described in PCT/US07/82563, filed Oct. 17, 2007, includes ingestible compositions such as pharma-informatics enabled compositions. The controlled activation ingestible identifiers include a controlled activation element that provides for activation of the identifier in response to the presence of a predetermined stimulus at a target site of interest.

Figure 3:
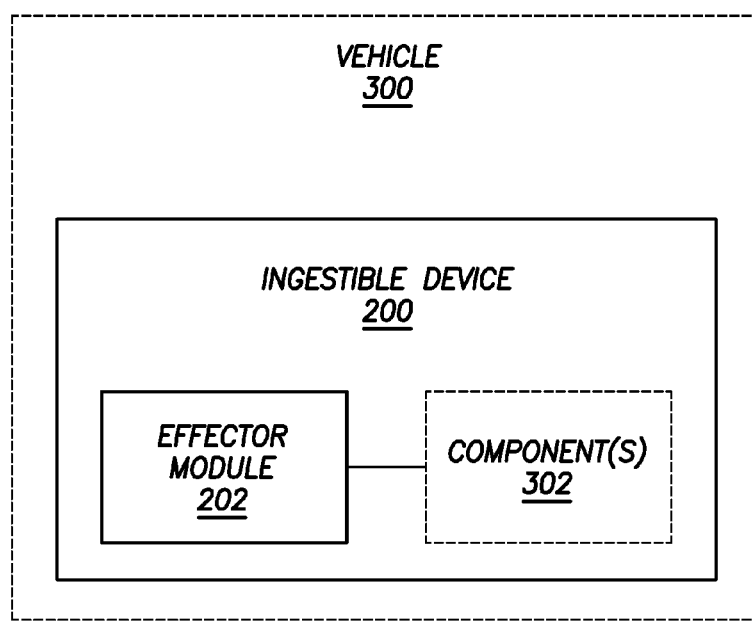
FIG. 3 illustrates an ingestible device of the therapy activator of FIG. 2 in greater detail.

FIG. 3 illustrates the ingestible device 200 of the therapy activator of FIG. 2 in greater detail. More particularly, the ingestible device 200 may be associated with various vehicles 300, e.g., placebo, medication, capsules, etc., as heretofore discussed. In various aspects, multiple ingestible devices 200 may be associated with a single vehicle 300, e.g., two ingestible devices 200 may be included in a single capsule; three or more ingestible devices 200 may be affixed on/manufactured within a pill, etc. In addition to the effector module 202, the ingestible device may comprise, be wholly or partially integrated with, integral to, etc., various other components 302. Examples of various other components 302 include modules for detection of physiological parameters of the subject. The effector module 202 comprises any device, component, hardware, and/or software, and combinations thereof, capable of receiving, processing, storing, generating, and/or communicating the effector instruction 204 of FIG. 2. In various aspects, for example, the effector module 202 may comprise an integrated circuit (IC), microcircuit, microchip, silicon chip, miniaturized electronic circuit, etc., having the processing capability to receive, generate, store, etc., and a means to forward, e.g., via a transmitter, etc., the effector instruction 204.

Figure 4:
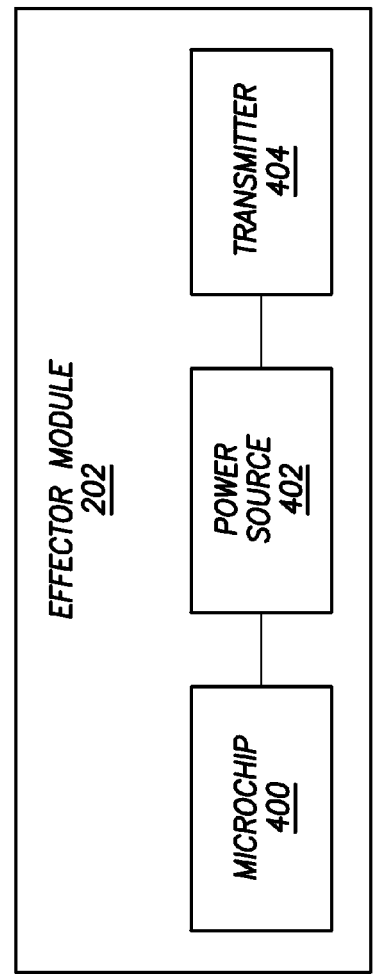
FIG. 4 illustrates an effector module of the ingestible device of FIG. 3 in greater detail.

FIG. 4 illustrates the effector module 202 of the ingestible device of FIG. 3 in greater detail. The effector module 202 may comprise a microchip 400, a power source 402, and a transmitter 404. The microchip 400 may be included and/or be associated with various components, e.g., software, storage devices, memory, processing instructions, etc., necessary to receive, generate, perform signal processing, and/or store the effector instruction 204.

The power source 402 may be variously configured, e.g., wet battery, etc. In one aspect, the power source 402 may be an incomplete power source, which may be activated upon contact with a targeted physiological site. Thus, the power source 402 gets activated, thereby powering the microchip 400. Stated differently, the power source 402 may exploit electrochemical reaction in an ionic solution such as gastric fluid, blood, or other bodily fluids and some tissues.

Depending on the configuration of the ingestible device 200, the target physiological site or location may vary, where representative target physiological sites of interest include, but are not limited to: a location in the gastrointestinal tract, such as the mouth, esophagus, stomach, small intestine, large intestine, etc. In certain aspects, the identifier is configured to be activated upon contact with fluid at the target site, e.g., stomach fluid, regardless of the particular composition of the target site. In some aspects, the identifier is configured to be activated by interrogation, following contact of the composition with a target physiological site. In some aspects, the identifier is configured to be activated at a target site, wherein the target site is reached after a specified period of time.

The microchip 400, in turn, forwards a signal incorporating the effector instruction 204 via the transmitter 404 to a destination, e.g., directly to the therapeutic device 108, to the therapeutic device 108 via the responder module 206, etc.

In various aspects, various modes of communication, channels of communication, and combinations thereof may be used. In one example, the effector instruction 204 may be communicated via a radio-frequency (RF) signal. In another example, the effector instruction 204 may be communicated via conduction, e.g., using in-body electrical signals as a communication vehicle. In still another example, the effector instruction 204 may be communicated via conduction to a receiver affixed externally to the patient, e.g., the responder module, which in turn, communicates the effector instruction to one or more therapeutic devices 108, e.g., implanted therapeutic devices via various modes of communication. Thus, as can be seen, various combinations of intra-body and extra-body channels and various modes of communication may be used.

The effector instruction 204 comprises any means capable of carrying the functionality as heretofore described, e.g., instigating an activation and/or modulation resulting in activation/modulation of a therapeutic device and/or therapy associated with the therapeutic device.

Figure 5:
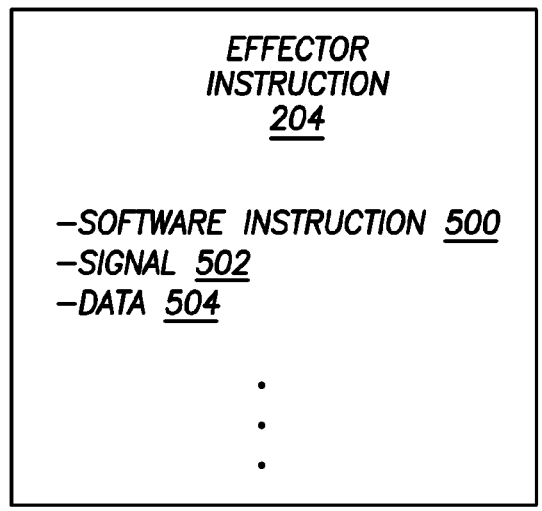
FIG. 5 illustrates an effector instruction of the ingestible therapy activator of FIG. 2 in greater detail.

FIG. 5 illustrates an effector instruction of the ingestible therapy activator of FIG. 2 in greater detail. In various aspects, the effector instruction 204 comprises any one or a combination of software instruction(s) 500, a signal 502, data 504, etc. Further, any or all of the foregoing may be variously embodied and may be communicated via various modes and channels, as heretofore discussed.

Figure 6:
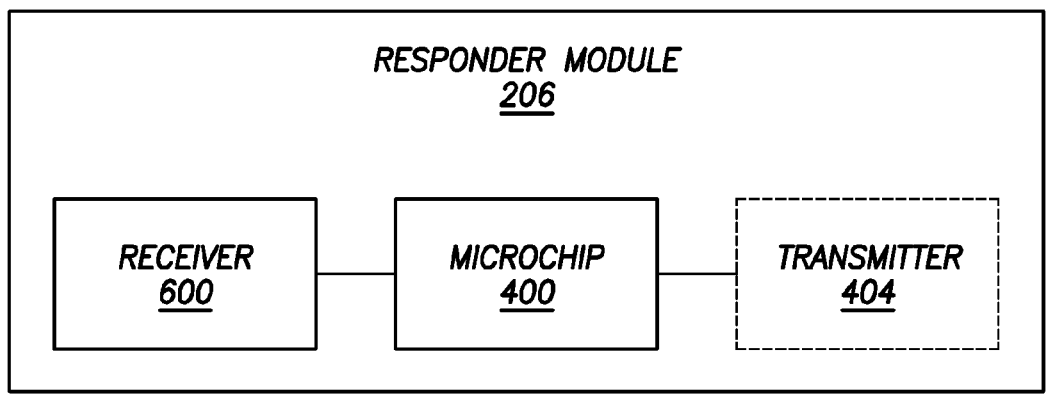
FIG. 6 illustrates a responder module of the ingestible therapy activator of FIG. 2 in greater detail.

FIG. 6 illustrates the responder module 206, which comprises any device, component, hardware, and/or software, and combinations thereof, capable of receiving, processing, storing, generating, and/or communicating the effector instruction 204. In various aspects the responder module 206 may be directly associated with a therapeutic device 108, e.g., in mechanical communication with the therapeutic device 108. Examples of such a responder module 204 include an instruction receipt and/or processing unit physically configured as a component of a cardiac device, a gastro-intestinal device, a lead device, an electrode device, etc.

In various aspects, the responder module 206 may be indirectly associated with the therapeutic device 108, e.g., may be in electrical communication with the therapeutic device 108 but not in mechanical communication therewith. Examples of such a responder module 204 include an instruction receipt and/or processing unit physically configured with/as a receiver, e.g., a wearable receiver such as a patch receiver, discussed in PCT/US2008/52845, supra.

FIG. 6 illustrates a responder module of the ingestible therapy activator of FIG. 2 in greater detail. In various aspects, the responder module 206 may comprise a receiver 600 to receive the effector instruction 204, a microchip 400 to process and/or store, etc., the effector instruction 204, and, optionally, a transmitter 404 to forward the effector instruction onward.

The receiver 600, for example, may be dedicated, i.e., receive only the effector instruction or may be universal, i.e., may receive signals, data, etc., in addition to the effector instruction. In the case of the universal receiver, such reception of multiple types of communications may provide for comprehensive device functionality, e.g., a cardiac pacing device which receives a pacing signal and the effector instruction.

Referring now to FIG. 4, the microchip 400, for example, may perform various processing activities with respect to the effector instruction. One example includes aggregating multiple effector instructions from one or more ingestible devices. Another example includes aggregating data from other sources, e.g., other devices, with the effector instruction. Another example includes modifying the effector instruction based on other data. To illustrate, the responder module 206 may receive and store data related to cardiac pacing from a cardiac device. For example, an effector instruction to slow the rate of the cardiac pacing from 70 beats per minute to 60 beats per minute. When the effector instruction is received, the microchip may analyze the data and, based on the result of the analysis, modify the effector instruction to slow the rate to 65 beats per minute. (After analysis of the data, this rate may be found preferable to the 65 beats per minute, as initially contemplated.) In this manner, the responder module 206 and the effector module 202 may co-operatively affect optimal therapies.

The transmitter 404, for example, may transmit the effector instruction(s) 204, data, or a combination thereof, to a destination device, e.g., the therapeutic device 108. The communication modes and channels may be of various types and combinations thereof, as heretofore discussed.

The therapeutic device 108 may be any device capable of providing or facilitating at least one medical therapy to a living being. Particularly, the therapeutic device 108 includes implantable devices.

Figure 7:
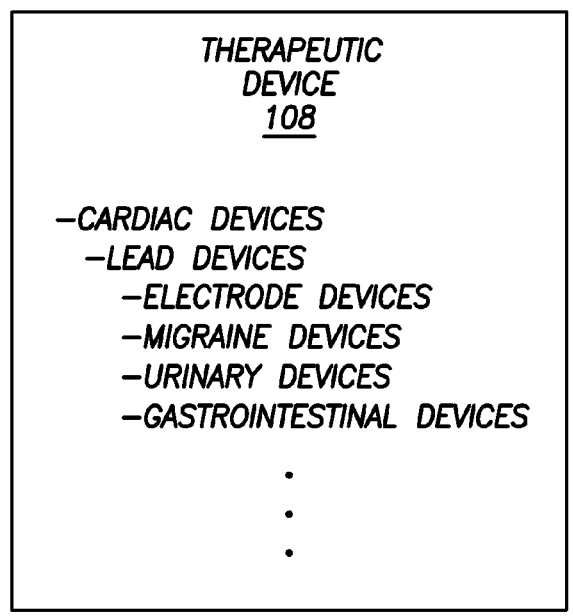
FIG. 7 illustrates a therapeutic device of the ingestible activator environment of FIG. 1.

FIG. 7 illustrates a therapeutic device of the ingestible activator environment of FIG. 1. The therapeutic device includes for example, cardiac devices, lead devices, electrode devices, migraine devices, urinary devices, gastrointestinal devices, etc.

The therapeutic devices may be activated and/or modulated in various ways, e.g., mechanical actuation, electrical activation, combinations thereof, etc. In one example of mechanical actuation, the effector instruction received by a gastro-intestinal device such as a gastric banding device (GBD) causes the GBD to signal controller circuitry associated with a clamping device of the GBD. The controller circuitry, in turn, generates the controls necessary to inflate the clamping device, thus constricting the esophagus which results in greater satiety, reduced ability to ingest food, improved gastric motility, etc.

In one example of an electrical activation, the effector instruction received by an electrode device such as a neural stimulation device (NSD) causes the NSD to signal controller circuitry associated therewith. The controller circuitry, in turn, generates the instructions necessary to provide electrical stimulation via the electrodes, thus masking pain, stimulating a cardiac contraction, etc.

FIG. 8 illustrates ingestion and activation of a therapeutic device via an ingestible therapy activator. As illustrated, ingestion of an ingestible therapy activator 200 by a human 800 results in activation of the ingestible therapy activator 200 by stomach fluids. Once activated, the ingestible therapy activator 200 transmits the effector instruction 204 to controller circuitry 808 associated with a cardiac pacing device 804. Upon receipt and processing of the effector instruction 204 by the controller circuitry 808, instructions are sent to the cardiac pacing device 804 that result in a change in the rate of pacing of the heart via the cardiac pacing device 804. In this manner, the patient can control, and ultimately optimize, certain features, aspects, and parameters of the patient's cardiac therapy.

Figure 9:
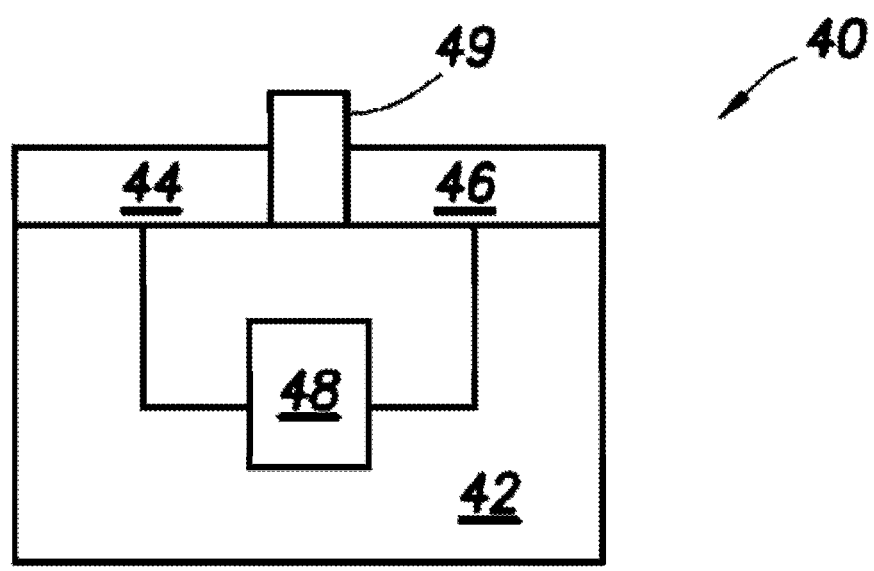
FIG. 9 is a block diagram representation of an event indicator system with dissimilar metals positioned on the same end and separated by a non-conducting material.

Referring now to FIG. 9, event indicator system 40 includes a framework 42. The framework 42 is similar to the framework 32 of FIG. 3. In this embodiment of the system 40, a digestible or dissolvable material 44 is deposited on a portion of one side of the framework 42. At a different portion of the same side of the framework 42, another digestible material 46 is deposited, such that materials 44 and 46 are dissimilar. More specifically, material 44 and 46 are selected such that they form a voltage potential difference when in contact with a conducting liquid, such as body fluids. Thus, when the system 40 is in contact with and/or partially in contact with the conducting liquid, then a current path, is formed through the conducting liquid between material 44 and 46. A control device 48 is secured to the framework 42 and electrically coupled to the materials 44 and 46. The control device 48 includes electronic circuitry that is capable of controlling part of the conductance path between the materials 44 and 46. The materials 44 and 46 are separated by a non-conducting skirt 49. Various examples of the skirt 49 are disclosed in U.S. Provisional Application No. 61/173,511 filed on Apr. 28, 2009 and entitled "HIGHLY RELIABLE INGESTIBLE EVENT MARKERS AND METHODS OF USING SAME" and U.S. Provisional Application No. 61/173,564 filed on Apr. 28, 2009 and entitled "INGESTIBLE EVENT MARKERS HAVING SIGNAL AMPLIFIERS THAT COMPRISE AN ACTIVE AGENT"; as well as U.S. application Ser. No. 12/238,345 filed Sep. 25, 2008 and entitled "IN-BODY DEVICE WITH VIRTUAL DIPOLE SIGNAL AMPLIFICATION"; the entire disclosure of each is incorporated herein by reference.

Continuing with further illustrations of the foregoing, effectuation of a neural stimulation device directed to migraine management, e.g., electrical stimulation of neural regions associated with migraine pain, may result in pain avoidance or abatement. If the ingestible device is taken at the onset of migraine aura, i.e., a sensory disturbance that often precedes a migraine headache, the patient may completely avoid the migraine headache and the severe pain associated therewith.

Effectuation of a urinary therapeutic device having electrodes to stimulate avoidance activity, which may assist in regulation of incontinence urges and issues.

Effectuation of an electrode device associated with penile erection may result in successful treatment of various impotence-related disorders, including erectile dysfunction.

Effectuation of various cardiac devices to activate/modulate cardiac therapies may result in any one or more of improved cardiac therapy, optimized cardiac therapy, diminished habituation, eliminated habituation, and avoidance of habituation.

Effectuation of an NSD associated with spinal cord stimulation prior to various physical activities may result in any one or more of improved pain-control therapy, optimized pain-control therapy, diminished habituation, eliminated habituation, and avoidance of habituation.

As a skilled artisan will note, various aspects facilitate at least some measure of control by the patient of the therapy.

The foregoing illustrate a few simple examples of the beneficial results associated the invention. The applications of the invention, as well as the resultant beneficial results, are too numerous to exhaustively list herein.

Various aspects include steps for ingesting an ingestible device having an effector module; sending an effector instruction via the effector module; and receiving and processing, via a responder module associated with a therapeutic device, the effector instruction, resulting in a response by the therapeutic device.

Various aspects include an ingestible therapy activator comprising an ingestible device having an effector module and an effector instruction.

Various aspects include a kit comprising an ingestible therapy activator and a therapeutic device. Further, kits may also include a responder module associated with at least one of the ingestible therapy activator and the therapeutic device.

One or more aspects of the subject invention may be in the form of computer readable media having programming stored thereon for implementing the various methods, or various steps thereof. The computer readable media may be, for example, in the form of a computer disk or CD, a floppy disc, a magnetic "hard card", a server, or any other computer readable media capable of containing data or the like, stored electronically, magnetically, optically or by other means. Accordingly, stored programming embodying steps for carrying-out the subject methods may be transferred or communicated to a processor, e.g., by using a computer network, server, or other interface connection, e.g., the Internet, or other relay means.

It is to be understood that this invention is not limited to particular aspects described, and, as such, may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference in their entirety as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A system for providing instructions to a therapeutic device, the system comprising:
   an ingestible unit comprising:
   a housing; and
   an effector module secured within the housing for providing an effector instruction,
   wherein the housing dissolves upon contact with the surrounding fluid of a desired target site to release the effector module and the effector module comprises a support structure including two dissimilar materials deposited thereon wherein the dissimilar materials represent a voltage potential difference and provide power for the ingestible unit upon contact with the fluid;
   a responder module in communication with the therapeutic device for receiving and processing the effector instruction, wherein the effector instruction alters at least an operation of the therapeutic device; and
   a hermetically sealed conductance control module electrically coupled to each of the dissimilar materials for controlling the conductance between the dissimilar materials to generate a unique current signature that presents the effector instruction, wherein the current signature is produced through controlled ionic emission.

2. The system of claim 1, wherein the ingestible unit further comprises an oral medication.

3. The system of claim 1, wherein the ingestible unit further comprises a second effector module secured within the housing to provide a second effector instruction.

4. The system of claim 1, wherein the effector instruction further comprises data.

5. The system of claim 1, wherein the responder module further comprises a transmitter to transmit at least one of data and signals.

6. The system of claim 1, further comprising the therapeutic device.

7. The system of claim 6, wherein the therapeutic device is a cardiac device.

8. The system of claim 7, wherein the cardiac device is a lead device.

9. The system of claim 6, wherein the therapeutic device is a selected from a group consisting essentially of an electrode device, a migraine device, a urinary device, and a gastrointestinal device.

10. The system of claim 1, wherein the responder module comprises at least one of a hardware component and a software component.

* * * * *